US011185585B2

(12) United States Patent
Carbonell et al.

(10) Patent No.: US 11,185,585 B2
(45) Date of Patent: Nov. 30, 2021

(54) METHODS AND COMPOSITIONS FOR IMPROVING ANTIANGIOGENIC THERAPY WITH ANTI-INTEGRINS

(71) Applicant: The Regents of the University of California, Oakland, CA (US)

(72) Inventors: Warren Shawn Carbonell, Burlingame, CA (US); Manish Kumar Aghi, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/869,970

(22) Filed: Jan. 12, 2018

(65) Prior Publication Data
US 2018/0236073 A1 Aug. 23, 2018

Related U.S. Application Data

(63) Continuation of application No. 14/006,669, filed as application No. PCT/US2012/030204 on Mar. 22, 2012, now abandoned.

(60) Provisional application No. 61/466,791, filed on Mar. 23, 2011.

(51) Int. Cl.
| A61K 39/00 | (2006.01) |
| A61K 39/395 | (2006.01) |
| C07K 16/22 | (2006.01) |
| C07K 16/28 | (2006.01) |
| A61K 49/00 | (2006.01) |

(52) U.S. Cl.
CPC ........ *A61K 39/39558* (2013.01); *A61K 49/00* (2013.01); *C07K 16/22* (2013.01); *C07K 16/2842* (2013.01); *A61K 2039/505* (2013.01); *A61K 2039/507* (2013.01); *A61K 2039/545* (2013.01); *C07K 2317/73* (2013.01); *C12N 2740/15043* (2013.01)

(58) Field of Classification Search
None
See application file for complete search history.

(56) References Cited

U.S. PATENT DOCUMENTS

| 4,816,567 A | 3/1989 | Cabilly et al. |
| 5,840,300 A | 11/1998 | Williams et al. |
| 5,846,536 A * | 12/1998 | Bissell ............... C07K 16/2842 424/158.1 |
| 6,033,665 A | 3/2000 | Yednock |
| 6,123,941 A * | 9/2000 | Bissell ............... C07K 16/2842 424/130.1 |
| 6,165,467 A | 12/2000 | Hagiwara et al. |
| 6,252,043 B1 | 6/2001 | Hession et al. |
| 6,596,276 B1 | 6/2003 | Senger et al. |
| 6,716,410 B1 | 4/2004 | Witztum et al. |
| 6,878,714 B2 | 4/2005 | Askew et al. |
| 6,949,245 B1 | 9/2005 | Sliwkowski et al. |
| 6,995,162 B2 | 2/2006 | Chen et al. |
| 7,618,627 B2 * | 11/2009 | Park ................... C07K 16/2842 424/130.1 |
| 8,246,952 B2 * | 8/2012 | Park ....................... A61P 35/00 424/130.1 |
| 2001/0003447 A1 | 6/2001 | Murai et al. |
| 2001/0016659 A1 | 8/2001 | Reidl et al. |
| 2002/0013774 A1 | 1/2002 | Morimoto |
| 2002/0165394 A1 | 11/2002 | Dumas et al. |
| 2003/0125339 A1 | 7/2003 | Chen et al. |
| 2003/0125359 A1 | 7/2003 | Lyons et al. |
| 2003/0143191 A1 | 7/2003 | Bell et al. |
| 2005/0038080 A1 | 2/2005 | Boyer et al. |
| 2006/0241115 A1 | 10/2006 | Potashman et al. |
| 2007/0248592 A1 | 10/2007 | Okano et al. |
| 2008/0108552 A1 * | 5/2008 | Hazlehurst ............. A61P 35/00 514/18.9 |
| 2009/0041767 A1 | 2/2009 | Ramakrishnan et al. |
| 2009/0220505 A1 | 3/2009 | Chuntharapai et al. |
| 2009/0124976 A1 | 5/2009 | Mittermeyer |
| 2009/0220504 A1 | 9/2009 | Chuntharapai et al. |

(Continued)

FOREIGN PATENT DOCUMENTS

| JP | 2007210968 | 8/2007 |
| WO | WO 2000041698 | 7/2000 |
| WO | WO 2000042012 | 7/2000 |

(Continued)

OTHER PUBLICATIONS

Tysnes et al Stimulation of Gliom-cell migration by laminin and inhibition by anti-α3 and anti-β1 integrin antibodies. (Int. J. Cancer, 67:777-784 (1996)). (Year: 1996).*
Hu et al. Angiopoietin-2 induces Glioma cell invasion by stimulating MMP-2 expression through the beta1 integrin and FAK signaling pathways. Neuro-Oncology 6, 307-399, 2004. Abstract# AN-10. (Year: 2004).*
Färber et al. An α5β1 integrin inhibitor attenuates glioma growth. Mol Cell Neurosci. Dec. 2008;39(4):579-85. (Year: 2008).*
Maglott et al. The α5β1 integrin is a therapeutic target for human glioblastoma and participates to chemoresistance. European Journal of Cancer, Supplement, (Jun. 2010) vol. 8, No. 5, pp. 55. Abstract No. 212. (Year: 2010).*

(Continued)

*Primary Examiner* — Maher M Haddad
(74) *Attorney, Agent, or Firm* — Shweta Chandra; Bozicevic, Field & Francis LLP

(57) ABSTRACT

Described here are methods and compositions for treating tumors and metastases that improve anti-angiogenesis therapy. By inhibiting these mechanisms in a biological system with an anti-beta one integrin composition in combination with an antiangiogenic composition, tumors and metastases may be deprived of an adequate blood supply, thereby resulting in tumor cell growth arrest and possibly regression, including tumor cell death. The present compositions comprise an anti-beta one integrin agent in combination with an anti-VEGF agent, in a pharmaceutical composition or compositions. Methods of treatment and of imaging are also described.

6 Claims, 11 Drawing Sheets

Specification includes a Sequence Listing.

(56) References Cited

U.S. PATENT DOCUMENTS

| | | |
|---|---|---|
| 2009/0304694 A1 | 12/2009 | Oliner et al. |
| 2010/0048677 A1 | 2/2010 | Mitchell et al. |

FOREIGN PATENT DOCUMENTS

| | | |
|---|---|---|
| WO | WO 2005117976 | 12/2005 |
| WO | WO 2007002543 | 1/2007 |
| WO | WO 2008060645 | 5/2008 |
| WO | WO 2009009114 | 1/2009 |
| WO | WO 2010072741 | 7/2010 |
| WO | WO 2010111254 | 9/2010 |

OTHER PUBLICATIONS

Brown et al. Regulatory effect of nerve growth factor in α9β1 integrin-dependent progression of glioblastoma. Neuro-Oncology 10, 968-980, 2008. (Year: 2008).*

Cordes et al. β1-integrin-mediated signaling essentially contributes to cell survival after radiation-induced genotoxic injury. Oncogene (2006) 25, 1378-1390. (Year: 2006).*

Kawataki et al. Laminin isoforms and their integrin receptors in glioma cell migration and invasiveness: Evidence for a role of α5-laminin(s) and α3β1 integrin. Exp Cell Res. Nov. 1, 2007;313(18):3819-31. (Year: 2007).*

Senger et al. The α1β1 and α2β1 Integrins Provide Critical Support for Vascular Endothelial Growth Factor Signaling, Endothelial Cell Migration, and Tumor Angiogenesis. American Journal of Pathology, vol. 160, No. 1, Jan. 2002. (Year: 2002).*

Alghisi GC, Ruegg C. Vascular integrins in tumor angiogenesis: mediators and therapeutic targets. Endothelium. 2006;13(2):113-135. (Year: 2006).*

Schiappacassi et al. p27Kip1 expression inhibits glioblastoma growth, invasion, and tumor-induced neoangiogenesis. Mol Cancer Ther 2008;7(5):1164-75. (Year: 2008).*

Wolterink et al., Therapeutic Antibodies to Human L1CAM: Functional Characterization and Application in a Mouse Model for Ovarian Carcinoma. Cancer Res; 70(6): 2504 Mar. 15, 2010. (Year: 2010).*

Zhu et al. Celastrol Acts as a Potent Antimetastatic Agent Targeting β1 Integrin and Inhibiting Cell-Extracellular Matrix Adhesion, in Part via the p38 Mitogen-Activated Protein Kinase Pathway. JPET 334:489-499, 2010. (Year: 2010).*

Wang et al Phenotypic Reversion or Death of Cancer Cells by Altering Signaling Pathways in Three-Dimensional Contexts (J Natl Cancer Inst 2002;94: 1494-1503). (Year: 2002).*

White et al. Targeted disruption of β1-integrin in a transgenic mouse model of human breast cancer reveals an essential role in mammary tumor induction. Cancer Cell : Aug. 2004 (6): 159-170. (Year: 2004).*

Park et al. β1 Integrin Inhibitory Antibody Induces Apoptosis of Breast Cancer Cells, Inhibits Growth, and Distinguishes Malignant from Normal Phenotype in Three Dimensional Cultures and In vivo. Cancer Res. Feb. 1, 2006; 66(3): 1526-1535. (Year: 2006).*

Stephens, L. E., et al., Deletion of B1 integrins in mice results in inner cell mass failure and peri-implantation lethality. Genes Dev, Aug. 1, 1995:9(151:1883-95.. (Year: 1995).*

Carter, Andrea., Integrins as Target: First Phase III Trial Launches, but Questions Remain. JNCI: Journal of the National Cancer Institute, vol. 102, Issue 10, May 19, 2010, pp. 675-677. (Year: 2010).*

Kuppermann B.D, Inhibition of α5β1 Integrin in Neovascular AMD—A Phase 1 Study. IOVS, (Apr. 2010) vol. 51, No. 13, pp. 1252. (Year: 2010).*

Google search for AIIB2 antibody, p. 1-2. Apr. 7, 2021 (Year: 2021).*

Bobo et al. "Convection-enhanced deliver of macromolecules in the brain", Proc. Natl. Acad. Sci., vol. 91, pp. 2076-2080, 1994.

Carbonell et al. "131 integrin targeting potentiates antiangiogenic the growth of bevacizumab-resistant glioblastoma", Cancer Res; 73(10); 3145-54, 2013.

Carbonell et al. "The vascular basement membrane as "soil" in brain metastasis", PLoS ONE, vol. 4, Issue 6, 14 pages, 2009.

Carnevale et al. "Regulation of Postangiogenic Neovessel Survival by 131 and 133 Integrins in Collagen and Fibrin Matrices", J. Vase Res.44:40-50, 2007.

Chekenya et al. "The progenitor cell marker NG2/MPG promotes chemoresistance by activation of integrin-dependent PI3K/Akt signaling", Oncogene; 27, 5182-5194, 2008.

Chen "Context-dependent VEGF signaling: molecular regulation of vascular patterning during angiogenesis", University of California, Los Angeles. Dissertation, 235 pages, 2009.

Christofori "Changing neighbours, changing behauviour: cell adhesion molecule-mediated signalling during tumour progession", The EMBO Journal, vol. 22, No. 10 pp. 2318-2323, 2003.

ClinicaiTrials.gov. A Phase 1 b Study With Volociximab in Combination With Carboplatin, Paclitaxel, and Bevacizumab in First-line, Advanced Non-small Cell Lung Cancer (NSCLC). Identifier: NCT00666692. 2008.

CN Office Action, Application No. 2012800245968, dated Aug. 7, 2014.

European Search Report, Application No. EP 12760157, dated Dec. 8, 2014.

Friedlander et al. "Migration of Brain Tumor Cells on Extracellular Matrix Proteins in Vitro Correlates with Tumor Type and Grade and Involves alphav, and β1 Integrins", Cancer Research; 56:1939-1947, 1996.

Gura "Magic bullets hit the target", Nature, vol. 417, pp. 584-586, 2002.

Hall et al. "The alpha1/β1 and alpha6/β1 integrin heterodimers mediate cell attachment to distinct sites on laminin", The Journal of Cell Biology, vol. 110, pp. 2175-2184, 1990.

Hazlehurst et al. "Adhesion to ®bronectin via b1 integrins regulates p27kip1 levels and contributes to cell adhesion mediated drug resistance (CAM-DR)", Oncogene; 19:4319-4327, 2000.

Heino et al. "Regulation of cell adhesion receptors by transforming growth factor-beta", The Journal of Biological Chemistry, vol. 264, pp. 380-388, 1989.

Hemler et al. "Structure of the integrin VLA-4 and its cell-cell and cell-matrix adhesion functions", Immunological Reviews 14:45-65, 1990.

Holash et al. "Vessel cooption, regression, and growth in tumors mediated by angiopoietins and VEGF", Science, vol. 284, pp. 1994-1998, 1999.

International Search Report and Written Opinion, PCT/US12/30204, dated Jun. 29, 2012.

Jahangiri et al. "β1 integrin critical path to antiangiogenic therapy resistance and beyond", Cancer Research, vol. 74, No. 1, pp. 3-7, 2014.

JP Office Action, Patent Application No. 2014-501258, dated Feb. 9, 2016.

Kim et al. "Regulation of angiogenesis in vivo by ligation of integrin alpha5 β1 with the central cell-binding domain of fibronectin", The American Journal of Pathology, vol. 156, No. 4, pp. 1345-1362, 2000.

Mardor et al. "Convection-enhanced drug delivery: increased efficacy and magnetic resonance image monitoring", Cancer Res. 65:(15). pp. 6858-6863, 2005.

Mas-Moruno et al. "Cilengitide: the first anti-angiogenic small molecule drug candidate. Design, synthesis and clinical evaluation", Anti-Cancer Agents in Medicinal Chemistry, 10, 753-768, 2010.

Matsushita et al. "Neuropilin-1 interacts with integrin β1 and modulates pancreatic cancer cell growth, survival and invasion," Annual Meeting of the Japanese Cancer Association, vol. 67th, p. 195, 2008. (Abstract).

Miletic et al. "Anti-VEGF therapies for malignant glioma: treatment effects and escape mechanisms", Expert Opinion on Therapeutic Targets, vol. 13, No. 4, pp. 455-468, 2009.

Park et al. "β1 Integrin Inhibition Dramatically Enhances Radiotherapy Efficacy in Human Breast Cancer Xenografts", Cancer Res. 68(11):4398-4405, 2008.

(56) References Cited

OTHER PUBLICATIONS

Park et al. "β1 Integrin Inhibitory Antibody Induces Apoptosis of Breast Cancer Cells, Inhibits Growth, and Distinguishes Malignant from Normal Phenotype in Three Dimensional Cultures and In vivo," Cancer Research 66(3), pp. 1526-1535, 2006.

Petersen et al. "Interaction with basement membrane serves to rapidly distinguish growth and differentiation pattern of normal and malignant human breast epithelial cells", Proc. Natl. Acad. Sci., vol. 89, pp. 9064-9068, 1992.

Sathornsumetee et al. "Antiangiogenic therapy in malignant glioma: promise and challenge", Current Pharmaceutical Design, vol. 13, No. 35, pp. 3545-3558, 2007.

SATO "Anti-angiogenic drugs," Japanese Journal of Clinical Medicine, vol. 68, No. 10, pp. 1825-1829, 2010. (Abstract).

Scott et al. "Bevacizumab salvage therapy following progression in high-grade glioma patients treated with VEGF receptor tyrosine kinase inhibitors", Neuro-oncology, vol. 12, No. 6, pp. 603-607, 2010.

Tol et al. "Chemotherapy, Bevacizumab, and Cetuximab in Metastatic Colorectal Cancer", N. Engl. J. Med. 360:563-572, 2009.

Yang et al. "Embryonic mesodermal defects in 5 integrin-deficient mice", Development; 119:1093-1105, 1993.

\* cited by examiner (low, mid, high reflects proportion of cells in plate which are actively proliferating)

SEQUENCE LISTING

```
<160> NUMBER OF SEQ ID NOS: 2

<210> SEQ ID NO 1
<211> LENGTH: 3656
<212> TYPE: DNA
<213> ORGANISM: Homo sapiens

<400> SEQUENCE: 1
agcgggagtc gcggaacagc aggcccgagc ccaccgcgcc gggccccgga cgccgcgcgg      60
aaaagatgaa tttacaacca attttctgga ttggactgat cagttcagtt tgctgtgtgt     120
```

```
ttgctcaaac agatgaaaat agatgtttaa aagcaaatgc caaatcatgt ggagaatgta    180
tacaagcagg gccaaattgt gggtggtgca caaattcaac atttttacag gaaggaatgc    240
ctacttctgc acgatgtgat gatttagaag ccttaaaaaa gaagggttgc cctccagatg    300
acatagaaaa tcccagaggc tccaaagata taaagaaaaa taaaaatgta accaaccgta    360
gcaaaggaac agcagagaag ctcaagccag aggatattac tcagatccaa ccacagcagt    420
tggttttgcg attaagatca ggggagccac agacatttac attaaaattc aagagagctg    480
aagactatcc cattgacctc tactacctta tggacctgtc ttactcaatg aaagacgatt    540
tggagaatgt aaaaagtctt ggaacagatc tgatgaatga aatgaggagg attacttcgg    600
acttcagaat tggatttggc tcatttgtgg aaaagactgt gatgccttac attagcacaa    660
caccagctaa gctcaggaac ccttgcacaa gtgaacagaa ctgcaccagc ccatttagct    720
acaaaaatgt gctcagtctt actaataaag gagaagtatt taatgaactt gttggaaaac    780
agcgcatatc tggaaatttg gattctccag aaggtggttt cgatgccatc atgcaagttg    840
cagtttgtgg atcactgatt ggctggagga atgttacacg gctgctggtg ttttccacag    900
atgccgggtt tcactttgct ggagatggga acttggtgg cattgtttta ccaaatgatg    960
gacaatgtca cctggaaaat aatatgtaca caatgagcca ttattatgat tatccttcta   1020
ttgctcacct tgtccagaaa ctgagtgaaa ataatattca gacaattttt gcagttactg   1080
aagaatttca gcctgtttac aaggagctga aaaacttgat ccctaagtca gcagtaggaa   1140
cattatctgc aaattctagc aatgtaattc agttgatcat tgatgcatac aattcccttt   1200
cctcagaagt cattttggaa aacggcaaat tgtcagaagg agtaacaata agttacaaat   1260
cttactgcaa gaacggggtg aatggaacag gggaaaatgg aagaaaatgt tccaatattt   1320
ccattggaga tgaggttcaa tttgaaatta gcataacttc aaataagtgt ccaaaaaagg   1380
attctgacag ctttaaaatt aggcctctgg gctttacgga ggaagtagag gttattcttc   1440
agtacatctg tgaatgtgaa tgccaaagcg aaggcatccc tgaaagtccc aagtgtcatg   1500
aaggaaatgg gacatttgag tgtggcgcgt gcaggtgcaa tgaagggcgt gttggtagac   1560
attgtgaatg cagcacagat gaagttaaca gtgaagacat ggatgcttac tgcaggaaag   1620
aaaacagttc agaaatctgc agtaacaatg gagagtgcgt ctgcggacag tgtgtttgta   1680
ggaagaggga taatacaaat gaaatttatt ctggcaaatt ctgcgagtgt gataatttca   1740
actgtgatag atccaatggc ttaatttgtg gaggaaatgg tgtttgcaag tgtcgtgtgt   1800
gtgagtgcaa ccccaactac actggcagtg catgtgactg ttctttggat actagtactt   1860
gtgaagccag caacggacag atctgcaatg ccggggcat ctgtgagtgt ggtgtctgta   1920
agtgtacaga tccgaagttt caagggcaaa cgtgtgagat gtgtcagacc tgccttggtg   1980
tctgtgctga gcataaagaa tgtgttcagt gcagagcctt caataaagga gaaagaaag   2040 acacatgcac acaggaatgt tcctatttta acattaccaa ggtagaaagt cgggacaaat   2100
taccccagcc ggtccaacct gatcctgtgt cccattgtaa ggagaaggat gttgacgact   2160
gttggttcta ttttacgtat tcagtgaatg ggaacaacga ggtcatggtt catgttgtgg   2220
agaatccaga gtgtcccact ggtccagaca tcattccaat tgtagctggt gtggttgctg   2280
gaattgttct tattggcctt gcattactgc tgatatggaa gcttttaatg ataattcatg   2340
acagaaggga gtttgctaaa tttgaaaagg agaaaatgaa tgccaaatgg gacacgggtg   2400
aaaatcctat ttataagagt gccgtaacaa ctgtggtcaa tccgaagtat gagggaaaat   2460
```

```
gagtactgcc cgtgcaaatc ccacaacact gaatgcaaag tagcaatttc catagtcaca      2520
gttaggtagc tttagggcaa tattgccatg gttttactca tgtgcaggtt ttgaaaatgt      2580
acaatatgta taattttttaa aatgtttttat tattttgaaa ataatgttgt aattcatgcc    2640
agggactgac aaaagacttg agacaggatg gttattcttg tcagctaagg tcacattgtg      2700
cctttttgac cttttcttcc tggactattg aaatcaagct tattggatta agtgatattt      2760
ctatagcgat tgaaagggca atagttaaag taatgagcat gatgagagtt tctgttaatc      2820
atgtattaaa actgattttt agctttacaa atatgtcagt ttgcagttat gcagaatcca      2880
aagtaaatgt cctgctagct agttaaggat tgttttaaat ctgttatttt gctatttgcc      2940
tgttagacat gactgatgac atatctgaaa gacaagtatg ttgagagttg ctggtgtaaa      3000
atacgtttga aatagttgat ctacaaaggc catgggaaaa attcagagag ttaggaagga      3060
aaaaccaata gctttaaaac ctgtgtgcca ttttaagagt tacttaatgt ttggtaacttt     3120 ttatgccttc actttacaaa ttcaagcctt agataaaaga accgagcaat tttctgctaa      3180
aaagtccttg atttagcact atttacatac aggccatact ttacaaagta tttgctgaat      3240
ggggaccttt tgagttgaat ttatttatt atttttattt tgtttaatgt ctggtgcttt       3300
ctatcacctc ttctaatctt ttaatgtatt tgtttgcaat tttggggtaa gactttttttt     3360 atgagtactt tttctttgaa gttttagcgg tcaatttgcc tttttaatga acatgtgaag      3420
ttatactgtg gctatgcaac agctctcacc tacgcgagtc ttactttgag ttagtgccat      3480
aacagaccac tgtatgttta cttctcacca tttgagttgc ccatcttgtt tcacactagt      3540
cacattcttg ttttaagtgc ctttagtttt aacagttcac tttttacagt gctatttact      3600
gaagttattt attaaatatg cctaaaatac ttaaatcgga aaaaaaaaaa aaaaaa         3656
```

<210> SEQ ID NO 2
<211> LENGTH: 23
<212> TYPE: DNA
<213> ORGANISM: Homo sapiens

<400> SEQUENCE: 2

```
ttctggattg gactgatcag ttc                                                23
```

METHODS AND COMPOSITIONS FOR IMPROVING ANTIANGIOGENIC THERAPY WITH ANTI-INTEGRINS

CROSS-REFERENCE TO RELATED APPLICATIONS

This application is a continuation of Ser. No. 14/006,669 filed on Dec. 3, 2013, which is a national phase of PCT/US2012/030204 filed on Mar. 22, 2012; which claims the benefit of U.S. Provisional Patent Application No. 61/466,791 filed on Mar. 23, 2011, which is hereby incorporated by reference in its entirety.

STATEMENT OF GOVERNMENTAL SUPPORT

None.

REFERENCE TO SEQUENCE LISTING, COMPUTER PROGRAM, OR COMPACT DISK

The instant application contains a Sequence Listing which has been submitted in ASCII format via EFS-Web and is hereby incorporated by reference in its entirety. Said ASCII copy, created on Jan. 31, 2012, is named "479-100 Sequence Listing.txt" and is 5,287 bytes in size.

BACKGROUND OF THE INVENTION

Field of the Invention

The present invention relates to the field of therapeutic compositions and therapy for cancer, including metastatic cancer, especially therapy targeted towards tumor vascularization.

Related Art

Presented below is background information on certain aspects of the present invention as they may relate to technical features referred to in the detailed description, but not necessarily described in detail. That is, individual parts or methods used in the present invention may be described in greater detail in the materials discussed below, which materials may provide further guidance to those skilled in the art for making or using certain aspects of the present invention as claimed. The discussion below should not be construed as an admission as to the relevance of the information to any claims herein or the prior art effect of the material described.

Many molecules have been identified as having angiogenic properties. However, the most potent identified to date is vascular endothelial growth factor-A (VEGF-A). This is the target of the drug bevacizumab (a.k.a., Avastin® Genentech, South San Francisco, Calif.) which has shown clinical promise in patients with various late-stage cancers including colon and rectal [Hurwitz et al., New England Journal of Medicine 350:2335-2342 (2004)], breast [Miller et al., New England Journal of Medicine 357:2666-2676 (2007)], lung [Sandler et al., New England Journal of Medicine 355:2542-2550 (2006)], kidney [Escudier et al., The Lancet 379:2103-2111 (2007)] and brain [Friedman et al., Journal of Clinical Oncology, doi:10.1200/JCO.2008.19.8721 (2009)]. Drugs designed against VEGF-A receptors, as opposed to VEGF-A itself, have also shown similar promise in recent clinical trials.

Lucentis® (ranibizumab) is also a recombinant humanized anti-VEGF antibody. Ranibizumab binds to multiple VEGF-A isoforms. As an antibody fragment, ranibizumab is designed to be a small molecule with a molecular weight of 48 kD. It is packaged for intravitreal use, rather than intravenous or intratumor use.

VEGF-A is the most characterized, and perhaps most potent, member of a family of vascular growth factors [Ferrara and Gerber, Acta Haematologica 106:148-156 (2002)]. Currently, other members include VEGF-B, VEGF-C, VEGF-D, VEGF-E, VEGF-F, and PlGF. These factors signal through at least three known receptor tyrosine kinases: VEGFR1, VEGFR2, and VEGFR3.

Unfortunately, the predictions of the anti-angiogenesis hypothesis thus far have not been realized in the clinic [Greenberg and Cheresh, Expert Opinion on Biological Therapy 9:1347-1356 (2009)]. At best, bevacizumab treatment in combination with chemotherapy results in prolongation of survival by a median of just 4.7 months [Hurwitz et al., New England Journal of Medicine 350:2335-2342 (2004)]. Patients ultimately succumb to continued cancer progression. The mechanism of this resistance is controversial and could reflect either an invalidation of the angiogenesis hypothesis or the ability of tumor cells to acquire an alternate vascular source.

Treatment strategies in the art have too heavily relied on a singular concept of tumor vascularization based on angiogenesis. The clinical resistance to anti-angiogenesis therapy is quite likely due to tumor cells utilizing an alternative method for obtaining a vasculature. Various types of tumor vascularization processes have been described including vessel ectasia, vessel remodeling, vessel co-option, vascular intussusception, vascular glomeruloid formation, pseudovessel formation, and circulating endothelial progenitors [reviewed in Dome et al., American Journal of Pathology 170:1-15 (2007)].

Several strategies in the art have proposed combination therapeutic strategies for inhibition of tumor vascularization. However, these strategies target only the angiogenic aspect of tumor vascularization or propose targeted vascular disruption of new tumor vessels. So far, no therapeutic strategy in the prior art provides for the complete inhibition of tumor and/or metastasis vascularization by administration to a biological system compounds targeting both angiogenic growth signaling and adhesion-based signaling of co-option in combination.

Specific Patents and Publications

Park et al, (U.S. Pat. No. 7,618,627 issued Nov. 17, 2009, "Method of increasing radiation sensitivity by inhibition of beta-one integrin") used anti-beta one integrin antibody AIIB2 iii conjunction with ionizing radiation to increase apoptosis of tumor cells.

Theodore Yednock [U.S. Pat. No. 6,033,665 (2000)] "Compositions and methods for modulating leukocyte adhesion to brain endothelial cells." This is one of the first patents resulting in an anti-integrin therapeutic which has been FDA approved for clinical use (Tysabri® against alpha-4-beta-1 for treatment of multiple sclerosis, Elan Pharmaceuticals, Inc.). Friess et al. [U.S. patent application Ser. No. 00/50, 385 A1 (2008)] proposed combination treatment with an anti-VEGF antibody and an anti-HER2 antibody, both targeting growth factors related to angiogenesis.

Senger et al. [U.S. Pat. No. 6,596,276 (2003)] proposed administration of inhibiting antibodies against alpha-1 and/or alpha-2 integrin subunits to target these downstream effectors of
VEGF mediated angiogenesis.

Bissell et al. [U.S. Pat. No. 5,846,536 (1998) and U.S. Pat. No. 6,123,941 (2000)] disclose a method for reversing malignant phenotype in tissue by administering an effective amount of a $\beta_1$ integrin function-blocking antibody or a peptide inhibitor of integrin function to the $\beta_1$ integrin receptors of tissue in need of such treatment.

BRIEF SUMMARY OF THE INVENTION

The following brief summary is not intended to include all features and aspects of the present invention, nor does it imply that the invention must include all features and aspects discussed in this summary.

The present invention comprises, in general, pharmaceutical compositions for inhibiting tumor cell growth, comprising: a first agent which is an inhibitor of VEGF activity, such as VEGF signaling and/or binding to the VEGF receptor; and a second agent which blocks beta-1 integrin. The blocking of beta-1 integrin can be blocking of cell attachment, blocking of beta-integrin intracellular signaling that occurs after cell attachment, or both. The agents used are compositions of matter, such as peptides or small molecules. They may be antibodies or antibody-like molecules. The combination of agents has a synergistic effect, i.e. is more effective than either agent separately. The agents may be in a single composition or a matched pair of compositions.

In certain aspects, the present invention comprises methods for inhibiting tumor cell growth. In general, the present methods include methods for inhibiting tumor cell growth, comprising the step of administering to a subject having said tumor: a combination of a first agent which is anti-angiogenic agent; and a second agent which blocks tumor cell interactions with the extracellular matrix mediated by beta-1 integrin and beta-1 integrin signaling, whereby tumor cell growth is inhibited to an extent greater than inhibition caused by either the first agent or the second agent alone, i.e. synergistically. Preferably the subject is a human subject with a tumor.

In one embodiment, the present method comprises administration of doses of an anti-beta-1 integrin antibody in conjunction with an antagonistic anti-VEGF receptor, anti-VEGF, (e.g. anti-VEGF-A) antibody. Various anti-VEGF and anti-integrin agents are described in further detail below. Methods for delivery of combined antibodies to a patient will be well known to those with ordinary medical, nursing, or allied health skill in the field of clinical oncology. The present compositions may be administered via any clinical means, especially parenteral or intratumoral injection. The present compositions can also be directly applied to an actual or potential cavity in the body including the tumor bed following surgical resection. Agents which increase the vascular permeability may also be administered at a clinically appropriate interval. These may enhance delivery of therapeutics in certain organs such as the central nervous system (CNS). In addition, adjuvant therapy regimens may be given prior to, during, or following treatment including radiation and chemotherapy. Repeat administrations of the embodiment may be provided to achieve the desired clinical effect.

DETAILED DESCRIPTION OF THE PREFERRED EMBODIMENT

Definitions

Figure 1A:
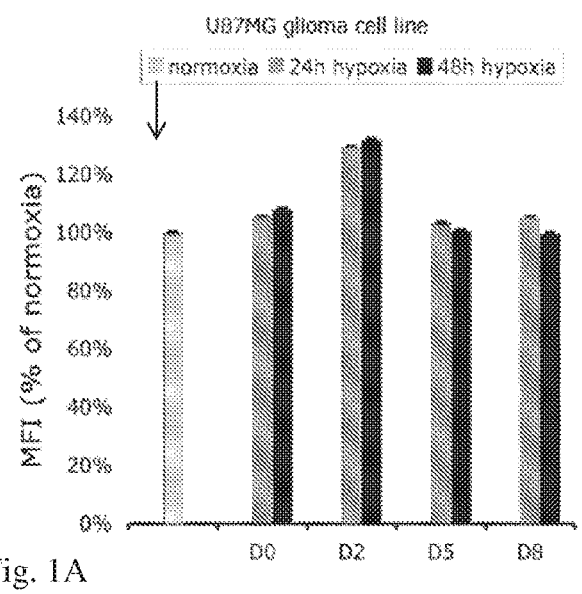
FIGS. 1A, 1B, and 1C is a series of three bar graphs showing increases beta-1 integrin (MFI) of U87MG glioma cells (1A), MDA-MB-231 breast carcinoma cells (1B) and SW1080 colorectal carcinoma cells (1), respectively in response to acute hypoxic insult.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

"VEGF" refers to vascular endothelial growth factor, also referred to as vasoendothelial growth factor, having an exemplary amino acid sequence at Genbank Accession Number AAA35789, described further at Leung, et al. "Vascular endothelial growth factor is a secreted angiogenic mitogen," Science 246 (4935), 1306-1309 (1989). VEGF is a dimeric, disulfide-linked 46-kDa glycoprotein related to Platelet-Derived Growth Factor ("PDGF"). It is produced by normal cell lines and tumor cell lines; is an endothelial cell-selective mitogen; shows angiogenic activity in in vivo test systems (e.g., rabbit cornea); is chemotactic for endothelial cells and monocytes; and induces plasminogen activators in endothelial cells, which are involved in the proteolytic degradation of the extracellular matrix during the formation of capillaries. A number of isoforms of VEGF are known, which, while they show comparable biological activity, differ in the type of cells that secrete them and in their heparin-binding capacity. The cellular receptors of VEGFs (VEGFRs) are transmembranous receptor tyrosine kinases. They are characterized by an extracellular domain with seven immunoglobulin-like domains and an intracellular tyrosine kinase domain. Various types of VEGF receptor have been characterized, including VEGFR-I (also known as flt-1), VEGFR-2 (also known as KDR3) and VEGFR-3. A large number of human tumors, especially gliomas and carcinomas, express high levels of VEGF and VEGFRs. This has led to the hypothesis that VEGF released by tumor cells stimulates the growth of blood capillaries and the proliferation of tumor endothelium in a paracrine manner and, through the improved blood supply, accelerates tumor growth.

The term "VEGF inhibitor" refers to a substance or method that decreases signaling by the VEGF-VEGFR pathway. VEGF inhibitors can be, for example, small molecules, peptides, polypeptides, proteins, including more specifically antibodies, including anti-VEGF antibodies, anti-VEGFR antibodies, intrabodies, maxibodies, minibodies, diabodies, Fc fusion proteins such as peptibodies, receptibodies, soluble VEGF receptor proteins and fragments, and a variety of others. A presently preferred VEGF inhibitor is a peptide, such as an antibody based inhibitor. Many VEGF inhibitors work by binding to VEGF or to a VEGF receptor. Others work more indirectly by binding to factors that bind to VEGF or to a VEGF receptor or to other components of the VEGF signaling pathway. Still other VEGF inhibitors act by altering regulatory posttranslational modifications that modulate VEGF pathway signaling. VEGF inhibitors in accordance with the invention also may act through more indirect mechanisms. Whatever the mechanism involved, as used herein, a VEGF inhibitor decreases the effective activity of the VEGF signaling pathway in a given circumstance over what it would be in the same circumstance in the absence of the inhibitor. Another VEGF inhibitor is nucleic acid based, using RNAi, as described below.

The term "humanized" refers to forms of non-human (e.g., rodent) antibodies which are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332: 323-329(1988); and Presta, Curr. Op. Struct. Biol. 2:593-596 (1992).

The term "convection enhanced delivery" refers to a method for drug delivery to the brain by overcoming the blood-brain barrier. Convection enhanced delivery was first described by R, Hunt Bobo et al in *Proc. Natl. Acad, Sci. USA* (March 1994, Vol 91, pages 2076-2080; "Convection-enhanced delivery of macromolecules in the brain"). Convection-enhanced delivery involves the stereotactic placement through cranial burr holes of several catheters into brain parenchyma and the subsequent infusion of therapeutic agents via a microinfusion pump. Standard methods of local delivery of most drugs into the brain, either by intravenous injection and passage through the blood brain barrier, or intraventricular injection, have relied on diffusion, which results in a nonhomogenous distribution of most agents. Intravenous administration of drugs to the brain is hampered by the blood-brain barrier, which prevents the passage of large molecules. The blood-brain barrier is characterized by tight junctions between vascular endothelial cells, which prevent or impede various naturally occurring and synthetic substances (including anti-cancer drugs) from entering the brain. In contrast to techniques that rely on diffusion, convection-enhanced delivery uses a pressure gradient established at the tip of an infusion catheter to push a drug into the extracellular space. The intention is to distribute the drug more evenly, at higher concentrations, and over a larger area than when administered by diffusion alone. Convection-enhanced delivery of therapeutic agents may occur after craniotomy with tumor resection. Convection enhanced delivery of drugs is described in detail by Yael Mardor et al. in *Cancer Research* (August 2005, vol 65, pages 6858-6863; "Convection-enhanced drug delivery: Increased efficacy and magnetic resonance image monitoring").

The term "human monoclonal antibody" refers to an antibody substantially free of non-human (e.g. mouse) sequence. It may be fully human, or humanized, as is known in the art, by the removal of mouse sequences save for the binding regions of the antibody, either the Fv portion or the CDR regions.

The term "antibody" further includes various forms of modified or altered antibodies, such as various fragments such as an Fv fragment, an Fv fragment containing only the light and heavy chain variable regions, an Fv fragment linked by a disulfide bond (Brinkmann, et al. Proc. Natl. Acad. Sci. USA, 90: 547-551 (1993)), a Fab or (Fab)'2 fragment containing the variable regions and parts of the constant regions, a single-chain antibody and the like (Bird et al., Science 242: 424-426 (1988); Huston et al., Proc. Nat. Acad. Sci. USA 85: 5879-5883 (1988)). The antibody may be originally of animal (especially mouse or rat) or human origin or may be chimeric (Morrison et al., Proc Nat. Acad. Sci. USA 81: 6851-6855 (1984)). It may be humanized as described in Jones et al., Nature 321: 522-525 (1986), and published UK patent application #8707252.

The term "extracellular substrate" refers to a substrate for cell binding, and may include both defined tissue such as vasculature (vascular endothelial cells) or extracellular matrix (ECM), that is, the extracellular part of animal tissue that usually provides structural support to the animal cells in addition to performing various other important functions; it is composed of an interlocking mesh of fibrous proteins and glycosaminoglycans.

The term "shRNA" refers to short hairpin RNA.

The term "RNAi" refers to RNA interference. RNAi is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. Cell 101, 25-33 (2000). Tuschl, T. et al. Genes Dev. 13, 3191-3197 (1999); Cottrell. T R, and Doering T L. 2003. Trends Microbiol. 11:37-43; Bushman F. 2003. Mol Therapy. 7:9-10; McManus M T and Sharp P A. 2002, Nat Rev Genet. 3:737-47). The process occurs when an endogenous ribonuclease cleaves the longer dsRNA into shorter, 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs or Ambion. In one embodiment one or more of the chemistries described herein for use in antisense RNA can be employed in molecules that mediate RNAi.

The term "pharmaceutical composition" refers to a product or pair of products containing the recited therapeutic agents in a specified amount in combination with pharmaceutically acceptable diluents, stabilizers, excipients, etc. The term "pharmaceutically acceptable" refers to molecular entities and compositions that are of sufficient purity and quality for use in the formulation of a pharmaceutical composition, medicine or medicament of the present invention and that, when appropriately administered to an animal or a human, do not produce an adverse, allergic or other untoward reaction. Since both human use and veterinary use are equally included within the scope of the present invention, a pharmaceutically acceptable formulation would include a pharmaceutical composition, medicine or medicament for either human or veterinary use.

In certain aspects of the present invention pertaining, to methods, a pharmaceutical composition may contain a single agent, but, according to the method, be administered. during a course of treatment, with the other agent.

General Methods and Materials

Described here are improved methods and compositions for treating tumors and metastases that recognize the dual mechanisms of tumor vascularization by 1) new growth or remodeling of vessels (i.e., angiogenesis) in combination with 2) utilization of existing vessels via a direct adhesive interactions (i.e., co-option). By inhibiting both mechanisms in a biological system in combination, tumors and metastases may be deprived of an adequate blood supply resulting in tumor cell growth arrest and possibly regression, including tumor cell death. The methods have a variety of uses in scientific research and health care wherein vascularization is a contributing factor in disease processes, especially cancer. in another embodiment, enhancement of vascularization for repair or replacement of tissue may be achieved by potentiating both angiogenesis and adhesive vessel co-option simultaneously or sequentially.

Current antiangiogenic therapies targeting the VEGF pathway are a rapidly growing market led by Genentech's Avastin® (bevacizumab) with $6.1 billion in total sales in 2009. However, Avastin® has only shown modest clinical success. At best it increases overall survival by 4.7 months in colon cancer and progression free survival by 4.2 months in brain cancer (gliobastoma multiforme, GBM). Even more discouraging, the FDA is considering overturning their approval for the use of Avastin® in metastatic breast cancer as has already occurred in the UK.

Avastin® is thought to work by preventing new vessel formation (angiogenesis) thus starving tumor cells of glucose and oxygen. Notably, beta-1 integrin is upregulated during oxygen deprivation (a.k.a., hypoxia) in tumor cells. In GBM cells taken from patients who have failed Avastin® therapy this target is upregulated 50 to 200× compared to untreated primary GBM cells. Interestingly, it is also upregulated during the process of tumor cell proliferation and after gamma irradiation suggesting a dual role in mitosis and cell survival. Inhibition of this target may also prevent integrin-dependent invasion of tumor cells upon ECM scaffolds (e.g., stroma and vascular basement membranes).

An aspect of the present invention involves use of agents that inhibit beta-1 integrin in patients who have failed treatment with anti-VEGF antibodies, such as Avastin® (bevacizumab). This has been shown in vitro as described below, and in vivo. The phrase "failed anti VEGF antibody treatment" is used here in its clinical sense. The clinical definition of bevacizmab failure is: 1) non response from the start (usually 70% of patients) and 2) disease progression in the face of therapy after initial response. There are various objective clinical criteria for progression, but the one most often used (and specifically used in the Bevacizmab clinical trials) are the McDonald Criteria. Patients in either group are usually taken off Bevacizmab and then reoperated on (28 days later as Bevacizmab makes you prone to bleeding) and submitted for possible third-line therapies or end of life care. Therefore, it is believed that anti-beta-1 compositions can be a monotherapy for 3L GBM who have failed Bevacizmab.

Vascular Co-option

Holash et al. (1999; Science 284: 1994-1998 "vessel co-option, regression and growth in tumors mediated by angiopoietins and VEGF") demonstrated in rat glioma model that a subset of tumors initially grew by co-opting existing host blood vessels. This co-opted host vasculature in due course showed up-regulation of VEGF and angiogenesis. The present inventor's studies on brain metastasis have shown that vascular co-option or the utilization of pre-existing vessels is the predominant form of vessel use by tumor cells during early experimental brain metastasis establishment and in human clinical specimens reflecting early stages of the disease. The findings exclude a requirement for de novo angiogenesis prior to microcolony formation. The CNS parenchyma is largely devoid of non-vascular stromal basement membrane components which are necessary for epithelial and carcinoma cell adhesion and survival. Vascular co-option, therefore, supplies substrates for malignant growth of non-neural carcinoma cells not otherwise widely available in the neuropil. Proliferation by metastatic tumor cells is highly potentiated upon adhesion to a basement membrane substratum and is attenuated by inhibiting MEK in vitro. Consistent with the experiments in tissue culture, during the early stages of colony formation in vivo the vast majority of micrometastases were found to be in direct contact with the VBM of existing brain vessels and many of these cells were proliferating. Thus the vascular basement membrane (VBM) is implicated as the active substrate for tumor cell growth in brain. VBM promoted adhesion and invasion of malignant cells and was sufficient for tumor growth prior to any evidence of angiogenesis.

The Role of Beta-1 Integrins in Vascular Co-option

Tumor cell adhesion to the vascular basement membrane of blood vessels is found to be mediated by beta-1 integrin. Blockade or loss of the beta-1 integrin subunit in tumor cells prevented adhesion to vascular basement membrane and attenuated metastasis establishment and growth in vivo. The requirement of metastatic carcinoma cells for the vasculature in adhesion and invasion during metastasis in the brain may be more analogous to the requirement for VBM during development of pancreatic islets. Islet cells use β1 integrins to interface with the VBM and this interaction is required for proliferation and endocrine function. Nikolova et al. termed this basement membrane microenvironment, a "vascular niche" (Nikolova et al., 2006; Dev Cell 10: 397-405; "The vascular basement membrane: a niche for insulin gene expression and beta cell proliferation"). Similarly vascular mural cells require the β1 integrin subunit for proper adhesion to vessels and for maintaining vessel stability. In an analogous fashion, carcinoma cells, then, appear to hijack the brain's VBM for essential functions during brain metastasis. Interestingly, inhibiting angiogenesis in circumscribed, well-established CNS melanoma metastases causes reversion to growth by vascular co-option. This suggests a continuum for vessel utilization by tumor cells which may represent a viable target for therapeutic exploitation.

The interaction between the tumor cells and the vessels relies on β1 integrin-mediated tumor cell adhesion to the vascular basement membrane of blood vessels. This interaction is sufficient to promote immediate proliferation and micrometastasis establishment of tumor lines in the brain. This angiotropic mechanism was universal to both carcinomas (anchorage-dependent cells) and lymphomas (anchorage-dispensible cells) in the CNS. β1 integrins play a dominant role in many facets of normal cell biology and have been implicated in cancer initiation, progression, and metastasis. There are at least 10 β1 integrin heterodimers which serve as variably promiscuous adhesive receptors to diverse ligands such as the collagens and laminins. Nonetheless our data suggest that antagonism of the β1 integrin subunit alone might be useful in therapeutic strategies for brain metastases. Indeed, Park et al. found that inhibitory anti-β1 integrin subunit antibodies induced apoptosis in breast carcinoma cells 110 grown in three dimensional culture, but not in cells grown in monolayers (Park et al. 2006; "β1 integrin inhibitory antibody induces apoptosis of breast cancer cells, inhibits growth, and distinguishes malignant from normal phenotype in three dimensional cultures and in vivo," *Cancer Res.* 66: 1526-1535). Treating mice hearing breast cancer xenografts from those cell lines with the same antibody led to decreased tumor volume. In addition to the apoptotic mechanism described in vitro, inhibition of vascular co-option may have also attenuated growth. In an alternative strategy to evaluate the role of β1 integrins, tumors were analyzed in the MMTV/PyMT transgenic model of breast cancer. Conditional deletion of β1 integrin after induction of tumorigenesis resulted in impairment of FAK phosphorylation and proliferation consistent with a reliance on anchorage-dependent signaling for tumor growth.

The present method is applicable for treatment of any type of epithelial or non-epithelial mammalian tumor having beta-1 integrin receptors, particularly, glioblastoma, anaplastic astrocytoma, breast/mammary carcinomas, lung carcinomas, melanomas, colon and rectal carcinomas, bladder carcinomas, endometrial carcinomas, ovarian carcinomas, renal carcinomas, Hodgkin and non-Hodgkin Lymphomas, pancreatic carcinomas, prostate carcinomas, and thyroid carcinomas.

Thus, an advantage of this aspect is that both mechanisms of tumor vascularization comprising angiogenesis and adhesive vessel co-option are targeted. As described below, an advantage of inhibition of beta-1 integrin is not only blocking co-option of blood vessels for use by a tumor, but also directly inhibiting tumor proliferation and preventing survival signaling pathways activated by hypoxia. This avoids therapeutic resistance identified in prior-art strategies relying only on anti-angiogenesis alone. The means for evaluation of treatment efficacy including tumor dormancy and regression will be well known to those with ordinary medical skill. These will include use of medical imaging techniques such as MRI, CT, PET, and SPECT as well as physical size measurements and clinical status of the patient. The two modalities of anti-angiogenesis agent and integrin-blocking agent together have a synergistic effect.

Antibodies to integrins, and, in particular, β1 integrin, useful in the practice of the present methods, are known in the art, See Bissell et al. U.S. Pat. No. 6,123,941 for a description of reverting malignant phenotype in cancer cells through application of anti-β1 integrin antibody AIIB2. Anti-beta-1 integrins against the CD-29 epitope are available from Research Diagnostics, Inc., Flanders, N.J. Another anti-β1 integrin antibody is CSAT, available from the University of Iowa Hybridoma Bank. Another commercially available anti-β1 integrin antibody is 4B7R, a Marine IgG1kappa antibody available from Atwell immunology Research Products.

AIIB2 is a rat monoclonal IgG1 that was originally isolated from a human choriocarcinoma hybridoma, and identified as an anti-β1 integrin antibody that non-specifically bound to all heterodimers of the β1 integrin extracellular domain. Experiments using F(ab)' fragments of enzyme-digested AIIB2 indicated that the epitope-binding portion of the antibody was active, and resulted in down modulation of β1 integrin mediated signaling and downstream signaling intermediates. Further details on β1 integrin biology is made more complex by 5 known splice variants that differ primarily with regard to the cytoplasmic domain, further described below in connection with polypeptides for immunization in preparing an anti-β1 integrin antibody. AIIB2 has been found to recognize all variants via the extracellular domain. Park et al (U.S. Pat. No. 7,618,627 issued Nov. 17, 2009, "Method of increasing radiation sensitivity by inhibition of beta-one integrin") used AIIB2 antibody in conjunction with ionizing radiation to increase apoptosis of tumor cells.

As reported in Hall et al., "The alpha 1/beta 1 and alpha 6/beta-1 Integrin Heterodimers Mediate Cell Attachment to Distinct Sites on Laminin," J. Cell Biol. 110:2175-2184 (1990) anti-integrin antibody AII B2 was prepared as follows: A Lewis rat was given two intraperitoneal injections 2 wk apart with 107 EDTA-harvested JAR choriocarcinoma cells, mixed 1:1 with Ribi adjuvant. 2 wk later, two additional intrasplenic injections were given 2 wk apart in the absence of adjuvant. A Balb/c mouse was given four bimonthly intraperitoneal injections of $5\times10^6$ first-trimester human cytotrophoblasts. 4 d after the last injection, each spleen was fused with Sp2/0 mouse plasmacytoma cells by the method of Kennett et al. (1980), as modified by Wheelock et al. (1987). Hybridoma supernatants were screened for their ability to inhibit JAR human choriocarcinoma cell attachment to FN, LN, or Col IV using the attachment assay described above. Two rat hybridoma supernatants were found that inhibited attachment to FN only (BIE5 and BIIG2), whereas two others inhibited attachment to LN, FN, and Col IV (AIIB2 and BIE11). One mouse hybridoma supernatant inhibited attachment of JAR cells to Col IV only (S2G3). These hybridomas were cloned by limiting dilution. The rat antibodies were purified from culture supernatants by affinity chromatography using goat anti-rat agarose. The mouse supernatant, S2G3, an IgM, was concentrated 10-fold by precipitation with 50% saturated ammonium sulfate at 4° C. These antibodies were retested for attachment inhibitory activity on FN, LN and Col IV coated substrates before further use.

An anti-integrin antibody suitable for use with the present method and composition may be produced by methods similar to those described in Werb, Z., Tremble, P., Berensten, O., Crowley, E., and Damsky, C. H. (1989). Signal transduction through the fibronectin receptors induces collagenase expression. J. Cell Biol. 109, 877-890; and Damsky, C. H., Fitzgerald, M., and Fisher, S. J. (1992). This provides a screening assay for potential antibodies. The immunogen used was whole human JAR choriocarcinoma cells. The antibody blocks cell attachment to Fn, Col-I, IV and LN, and so can be further characterized in these ways.

Inhibition of beta-1 integrin with the rat monoclonal antibody AIIB2 combined with hypoxia synergistically reduced growth of GBM cells in vitro. AIIB2also directly reduced growth of Avastin® evasive GBM cells in vitro. Such a composition might also be used for in vivo tumor imaging or as a biomarker for cell proliferation or responses to cell insults (e.g., hypoxia or ionizing radiation). Striking upregulation of beta-1 integrin in angiogenic blood vessels of untreated GBM was also observed. Therefore, it may also be useful for directly inhibiting and/or imaging the process of angiogenesis in vivo.

As stated above, a variety of VEGF inhibitors may be used in the present methods and compositions. As described in Oliner et al. US 2009/0304694 A1, published Dec. 10, 2009, entitled "ANG2 AND VEGF INHIBITOR COMBINATIONS," suitable VEGF inhibitors for use in the present methods include the following: (a) 4TBPPAPC, as described in US2003/0125339 or U.S. Pat. No. 6,995,162 which is herein incorporated by reference in its entirety, particularly in parts disclosing 4TBPPAPC; (b) AMG 706, as described in US2003/0125339 or U.S. Pat. Nos. 6,995,162,U.S. Pat. No. 6,878,714 which is herein incorporated by reference in its entirety, particularly in parts disclosing AMG 706; (c) Avastin®; (d) Nexavar®, as described in WO00/42012, WO00/41698, US2005/0038080A1, US2003/0125359A1, US2002/0165394A1, US2001/003447A1, US2001/0016659A1, and US2002/013774A1 which are herein incorporated by reference in their entirety, particularly in parts disclosing Nexavar®; (e) PTK/ZK; (f) Sutent®, and (g) VEGF inhibitors of Formula IV as described in US2006/0241115. In this regard, a presently preferred VEGF inhibitor is AMG 706.

Humanized anti-VEGF or anti-integrin antibodies can be prepared according to several methods. U.S. Pat. No. 6,949,245 to Sliwkowski et al., issued Sep. 27, 2005, entitled "Humanized anti-ErbB2 antibodies and treatment with anti-ErbB2 antibodies," described methods for humanizing an antibody that may be adapted according to the present teachings. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc) and human constant region sequences.

As further described in the above-referenced U.S. Pat. No. 6,949,245, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986);

Riechmann et al., Nature, 332:323-327 (1988); Verhoeyen et al., Science, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

Single chain recombinant antibodies may also be used, as described, for example in U.S. Pat. No. 5,840,300 to Williams et al, entitled "Methods and compositions comprising single chain recombinant antibodies," hereby incorporated by reference for purposes of describing methods useful in the preparation of such compositions. Briefly, Kappa, heavy, and lambda immunoglobulin chains are amplified separately and are subsequently combined as single chains, using recombinant PCR, i.e., the splicing by overlap extension (SOE) PCR method, wherein the single chains comprise a heavy chain plus a kappa chain or a heavy chain plus a lambda chain. Flexible linear-linker peptides are used in the primers which therefore comprise the linker used to join $V_L$ to $V_H$ to form the novel recombinant Fv fragments containing integrin binding variable regions comprising both light and heavy chains as a single chain. The Fv fragments may be developed as a library of Fv fragments directed against β1 integrin subunits.

Suitable antibodies can also be prepared in genetically engineered mice designed to express human antibodies. The mice can be immunized with an antigen comprising a fragment of human β1 integrin and the mouse splenocytes containing active B cells fused with a suitable myeloma line. Mice with the human Ig repertoire are commercially available. See Hemachandra et al., "Human Monoclonal Antibodies against *Pseudomonas aeruginosa* Lipopolysaccharide Derived from Transgenic Mice Containing Megabase Human Immunoglobulin Loci Are Opsonic and Protective against Fatal Pseudomonas Sepsis," INFECTION AND IMMUNITY, April 2001, p. 2223-2229 Vol. 69, No. 4.

Another technique for preparing the present antibodies, phage display combinatorial library technology, provides a useful method to generate large libraries of human Mabs that may be screened for anti-integrin activity. The libraries made from lymphocyte mRNA may consist of up to $10^8$ recombinants of monoclonal Fab repertoires. By displaying the library on a filamentous phage surface and panning against a model epitope (β1 integrin fragment as described below, monoclonal Fab antibodies can be selected and analyzed for their immunological properties and biological activities (integrin inhibition). Fabs are ideal for use in both therapeutic and diagnostic methods as they can be produced in large quantities inexpensively and they are innately nonimmunogenic. See U.S. Pat. No. 6,716,410 to Witzum et al. for a description of this technique, which is hereby incorporated by reference.

As described by Marks et al., a human single-chain Fv (scFv) may be isolated from a non-immune phage library which binds the β1 antigen. CDR3 of the light (V(L)) and heavy (V(H)) chain variable region of a selected antibody may then be sequentially mutated, the mutant scFv displayed on phage, and higher affinity mutants selected on antigen. See Schier et al., "Isolation of picomolar affinity anti-c-erbB-2 single-chain Fv by molecular evolution of the complementarity determining regions in the center of the antibody binding site," J Mol Biol. 1996 Nov. 8; 263(4): 551-67.

Bispecific antibodies (e.g. diabodies) which cross link with other antigens may also be employed. Unlike other bispecific formats, diabodies can be produced in functional form by secretion from bacteria (*E.coli*) or yeast (*P. Pastoris*). Detailed protocols can be found in: Tomlinson I. and Holliger P. (2000) Methods for generating multivalent and bispecific antibody fragments, *Methods Enzymol*, 326, 461-179; and Holliger, P. (2001) Expression of antibody fragments in Pichia pastoris. *Meth. Mol. Biol*. Dimeric antibody fragments, or minibodies, may be created in a variety of known ways. These produce noncovalent or covalent dimers (sc(FV)2). The present antibody composition may be prepared as a purified pharmaceutical composition with known stabilizers and excipients in a sterile powder or liquid form for intravenous administration as is known in the art and exemplified in the description of a freeze dried monoclonal antibody in U.S. Pat. No. 6,165,467, hereby incorporated by reference.

The term "'synergistic" is used herein in its conventional sense, referring to a combination of components wherein the activity of the combination is greater than the additive of the individual activities of each component of the combination.

Other inhibitors of VEGF activity may be used in the present methods and compositions. For example, Aflibercept (VEGF-Trap, AVE-0005) is a fully human recombinant fusion protein composed of the second Ig domain of vascular endothelial growth factor receptor 1 (VEGFR1) and the third Ig domain of vascular endothelial growth factor receptor 2 (VEGFR2), fused to the Fc region of human IgG1. Aflibercept binds to all VEGF-A isoforms as well as placental growth factor (PlGF), thereby preventing these factors from stimulating angiogenesis. Aflibercept is administered by intravenous infusion at 4 mg/kg every two weeks in combination with chemotherapy.

A VEGF receptor-binding protein, designated KDR-bp (KDR-binding protein), from the venom of the Eastern Cottonmouth (Agkistrodonpiscivoruspiscivorus) is a catalytically inactive PLA2 homologue, Lys49PLA2, which possesses potent myotoxicity, and is an exogenous molecule found to antagonize the VEGF receptor, as described in Fujisawa et al. "Catalytically inactive phospholipase A2 homologue binds to vascular endothelial growth factor receptor-2 via a C-terminal loop region," Biochem. J. (2008) 411, 515-522, In certain aspects, the present invention comprises a method for inhibiting tumor cell growth, comprising the step of administering to a subject having said tumor a combination of a low-dose first agent which is anti-angiogenic agent; and a second agent which blocks tumor cell binding mediated by beta-1 integrin, whereby tumor cell growth is inhibited to an equivalent amount as caused by the first agent at a higher clinical dose. The low-dose first agent may for example be a VEGF inhibitor which is administered at a minimum dosage as indicated on the product's labeling or literature. According to the present invention, tumor growth will be inhibited to at least the same extent as if the VEGF inhibitor were given at the highest approved dose. For example, the recommended dose of bevacizumab when treating colon or rectal cancer is either 5 mg or 10 mg per kg (about 2.3 mg to 4.5 mg per pound) given by IV every 14 days. The recommended dose will vary (either 5 or 10 mg per kg) based on the type of chemotherapy being given.

Therapeutic Combinations of an Agent is an Inhibitor of VEGF and an Agent which Blocks Beta-integrin Agents modulating adhesive vessel co-option and angiogenesis may be administered together or sequentially after a prescribed time interval. When administered together they may be delivered via an acceptable biocompatible delivery platform. This may be a nanoconjugate or polymer. Alternatively, the agents may directly fused to each other. In addition, multiple angiogenesis and/or adhesive vessel co-option modulating agents may be administered either simultaneously or sequentially. Finally, any of the embodiments may be combined with adjuvant therapies such as radiation, chemotherapy, and/or agents which increase vascular permeability.

Embodiments for inhibiting the angiogenesis signaling aspect having an inhibitory effect on VEGF-A, either in downstream signaling or in the ability to bind to its extracellular receptors (VEGFR-1/Flt-1, VEGFR-2/Flk-1), may be used. Other mediators of angiogenesis may also be targeted including other VEGF family members (VEGF-B, VEGF-C, VEGF-D, VEGF-E, and PlGF) and their receptors (VEGFR-1/Flt-1, VEGFR2/Flk-1, VEGFR-3/Flt-4), fibroblast growth factors (FGF-1 and FGF-2) and their receptors (FGFR-1, FGFR-2, FGFR-3, FGFR4), epidermal growth factor members (EGF and HB-EGF) and their receptor (EGER), CEACAM-1/CD-66a, the orphan receptor HER-2, angiopoietins (Ang1, Ang2, Ang3, and Ang4) and their receptors (Tie-1 and Tie2), platelet-derived growth factors (PDGF) and their receptors (PDGFR type alpha and PDGFR type beta), transforming growth factor-beta family members (TGF-beta-1, TGFbeta2, TGF-beta3) and their receptor (TGFBR2), delta-like ligand 4 and its receptor (Notch), and naturally occurring antiangiogenic fragments of pre-existing structural proteins such as angiostatin and tumstatin.

Embodiments for targeting the adhesive vessel co-option signaling aspect having an inhibitory effect on beta-1 integrin, either in downstream signaling or in the ability to hind to its extracellular receptors, may be used. These may include disintegrins, components/fragments of extracellular matrix, focal adhesion kinase (FAK), FAK-related non kinase, and extracellular signal-related kinase (ERK/MAPK).

The anti-angiogenic composition may comprise a human monoclonal antibody or antibody fragment, humanized antibody or antibody fragment, inhibitory peptide, kinase inhibitor, endogenous inhibitor, small molecule inhibitor, nanobody, RNAi, aptamer, antisense, or any of these agents in combination with a pharmaceutically acceptable vector or carrier.

The anti-adhesion-based vessel co-option composition may comprise a human monoclonal antibody or antibody fragment, humanized antibody or antibody fragment, inhibitory peptide, kinase inhibitor, endogenous inhibitor, small molecule inhibitor, nanobody, RNAi, aptamer, antisense, or any of these agents in combination with a pharmaceutically acceptable vector or carrier.

In a presently preferred embodiment, a patient with recurrent glioblastoma multiforme (GBM) will undergo implantation of one or more catheter(s) placed intratumorally, within a resection cavity, or subdurally. The patient will be administered standard bevacizumab therapy I.V. at a clinically-appropriate dose and interval. At least 24 hours, or ideally 48 to 120 hours, after bevacizumab injection an inhibitory anti-beta-1 integrin composition will be administered through said catheters via convection enhanced delivery (CED) device at a clinically-relevant dose and rate.

in another embodiment the above regimen be combined with an additional adjuvant therapy such as ionizing radiation and/or chemotherapy. In another embodiment, the above regimen will be administered to a newly diagnosed GBM. In another embodiment both the antiangiogenic composition and the inhibitory anti-beta-1 integrin composition will be administered via CED. In another embodiment both the antiangiogenic composition and the inhibitory anti-beta-1 integrin composition will be administered parenterally. In another embodiment, one or both compositions will be administered directly to the tumor bed in an inert carrier such as a dissolvable biocompatible polymer. In another embodiment, both compositions will be administered simultaneously as a bivalent antibody. In another embodiment, the inhibitory anti-beta-1 integrin composition will be administered alone to a patient who has failed prior antiangiogenic therapy. In another embodiment, the inhibitory anti-beta-1 integrin composition will be administered alone to a patient who is naïve to antiangiogenic therapy. In another embodiment, the anti-beta-1 integrin composition may further comprise a radioisotope attached thereto, particularly a beta-emitting element.

An alternative agent for inducing hypoxia, besides antiangiogenic therapy, is to use endovascular techniques for vessel embolization (superselective embolization/targeted embolization). This procedure is known for use for highly vascular brain lesions such as meningiomas and AVMs in order to shrink the lesion thus providing for more favorable circumstances for surgical resection.

Inhibiting this target may be effective against several cancers expressing beta1 integrins beyond GBM including most epithelial and non-epithelial tumors such as breast, lung, liver, kidney, colon, melanoma, and lymphoma. There may be an additional use for an anti-beta1 composition for inhibiting angiogenesis in non-neoplastic diseases such as age-related wet macular degeneration. Finally, there may be use for an anti-beta-1 composition for anti-inflammatory indications as beta-1 integrin signaling is important for some immune cell functions including adhesion and proliferation.

An alternate embodiment relates to potentiate vascularization in a biological system as in a regenerative medicine strategy. In such an embodiment, selective modulation of both angiogenesis and adhesive vessel co-option can result in improved tissue repair or regeneration.

A further embodiment of the present invention comprises the use of shRNA(short hairpin RNA) to knockdown beta-1 integrin gene expression in a tumor cell. This was carried out in an example below, where significant reduction in tumor cell growth was shown in a cell line resistant to an anti-VEGF antibody. In the exemplified work, ShRNAs are precursors to the short interfering RNAs (siRNAs) that are the powerful mediators of RNA interference (RNAi). In RNAi, genes homologous in sequence to the siRNA are silenced at the post-transcriptional state. There are a variety of different hairpin structures that may give rise to effective siRNAs. Lentiviruses, such as the human immunodeficiency virus (HIV) are capable of infecting non-dividing cells, including differentiated neurons of the brain. Short hairpin RNAs can be expressed from lentiviruses, allowing for high efficiency transfection of a variety of cell types. An effective RNA hairpin construct can be designed based on the sequence of the gene to be silenced. Integrin beta-1 is a protein that, in humans, is encoded by the ITGB1 gene. The entire human mRNA for integrin beta-1 subunit is set forth in Genbank locus X07979 and accession number BC020057. This sequence of 3656 nucleotides (SEQ ID NO: 1), also given in J. Cell Biol. 105 (3), 1183-1190 (1987) is not reproduced here for the sake of brevity, but is incorporated herein specifically by reference. This known sequence may be used to design interfering nucleic acid constructs such as the exemplified shRNA.

Although not every hairpin construct will produce an effective RNAi response, rules have been developed that enrich for successful constructs. These rules are based on the examination of large numbers of effective constructs and thermodynamic analysis of microRNAs and effective siRNAs. Rules are published for example at Ambion technical bulletin #506, available online.

The preparation of competent virus from DNA vectors involves packaging the construct into a cell line. Packaging an RNAi lentivirus is essentially the same as packaging a lentivirus carrying a cDNA. In essence, DNA vectors are transiently transfected into a packaging cell line—such as human 293 cells, and after 2-3 days the supernatant will contain the virus.

For the most part, lentiviral vector production systems are based on a "split" system, where the natural viral genome has been split into individual helper plasmid constructs. This splitting of the different viral elements into three or four separate vectors diminishes the risk of creating a replication-capable virus by adventitious recombination of the lentiviral genome.

When choosing a lentiviral production system for producing a beta integrin knockdown according to the present invention, one may prepare viruses that have a restricted host range (i.e. virus that may infect only rodents) vs. a broad host range (virus that may infect mouse, birds, human, etc). For the most part, the viral surface coat protein determines the species specificity. Because the lentiviral production systems are split, this coat protein can be switched by using, for example, the vesicular stomatitis virus (VSV/G) glycoprotein (which display a wide host range tropism) vs. an ecotropic maltose binding surface glycoprotein (which displays a limited specificity).

Using Gene link siRNA explorer (http colon slash slash www dot genelink.com/sirna/shrnai.asp), 483 shRNA sequences were identified as inhibitors of human beta-1 integrin mRNA, including, for example, the sequence TTCTGGATTGGACTGATCAGTTC (SEQ ID NO: 2).

The agents referred to here are preferably delivered to a patient in need thereof, which is, suffering from the tumors described here, in the form of a pharmaceutical composition suitable for human administration. The composition will comprise the agent, e.g. antibody or nucleic acid in isolated and substantially pure form, admixed with stabilizers, buffers, excipients, etc., as known in the art, and free of adventitious agents.

The examples below are illustrative of certain inventive concepts described here.

EXAMPLES

Example 1

Hypoxia Associated with High Beta-1 Integrin Expression

Figure 1B:
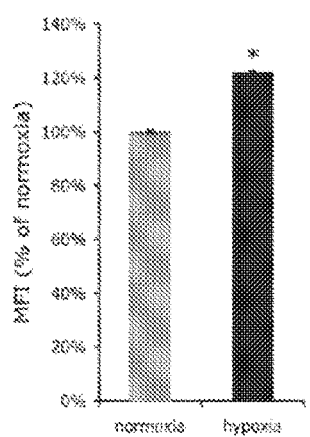
Figure 1C:
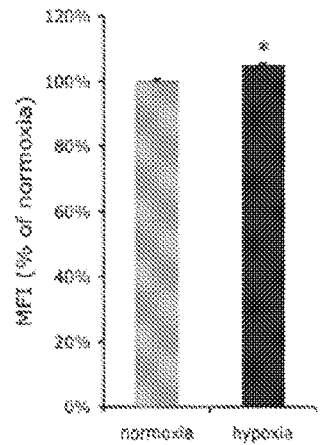
Figure 2A:
FIGS. 2A and 2B is a pair of photographs showing staining of glioma tumor xenografts for integrin beta 1 expression with (2A) and without (2B) treatment with bevacizmab treatment.
Figure 2B:

Here it is shown that hypoxia, another common cellular stress in the setting of fast-growing cancers and after antiangiogenic therapy, is correlated with high beta 1 expression in patient glioblastomamultiforme (GBM) specimens. To directly confirm this mechanism, we subjected glioma cells to 6 to 48h of 1% oxygen to simulate microenvironmental hypoxia. We observed a significant increase in beta 1 integrin expression in glioma cells in vitro (FIG. 1A). This is a rapid and reversible cellular response and was also demonstrated in breast and colorectal carcinoma cells (FIGS. 1B & 1C). To verify that anti-angiogenic therapy can acutely increase beta 1 expression in growing tumors in vivo we stained glioma tumors from mice taken within days of the last bevacizumab treatment. Marked increases in beta 1 were observed in the treated tumors compared to controls, particularly in the hypoxic tumor core (FIG. 2).

Example 2

Increased Beta 1 Integrin Expression Observed During Tumor Cell Proliferation

Figure 3A:
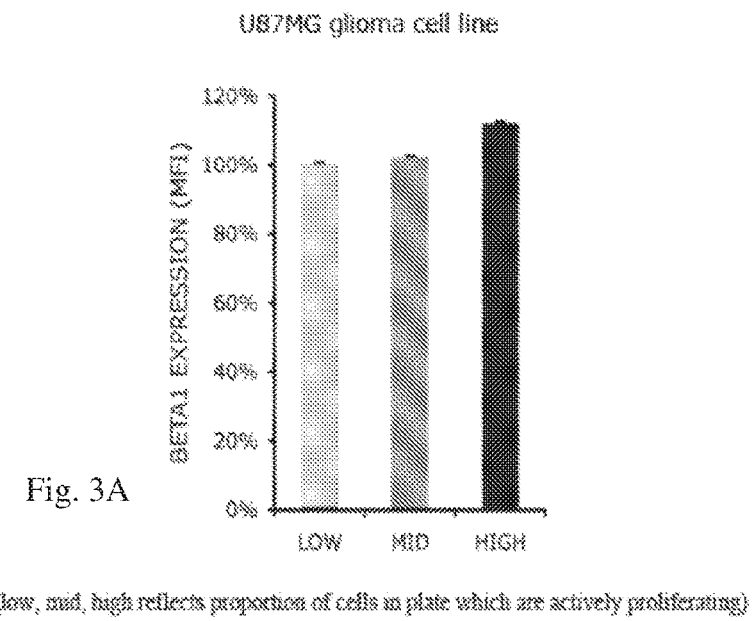
FIG. 3A is a bar graph showing integrin beta 1 expression in U87MG glioma cells in different conditions of proliferation.
Figure 3B:
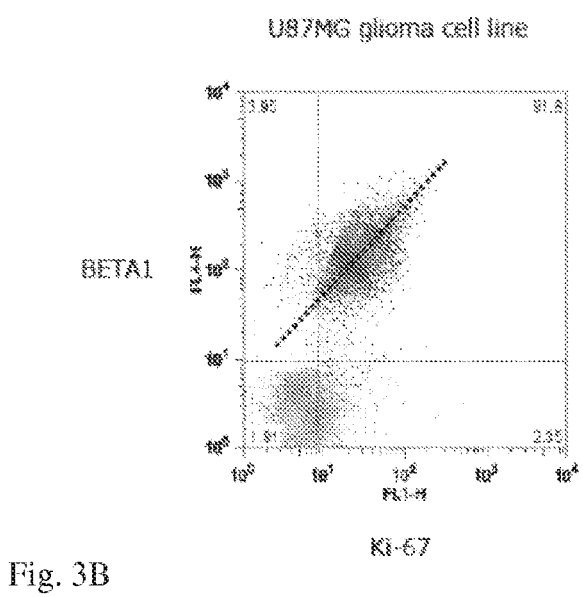
FIG. 3B is a scatter plot showing correlation between integrin beta 1 expression and proliferation.
Figure 4A:
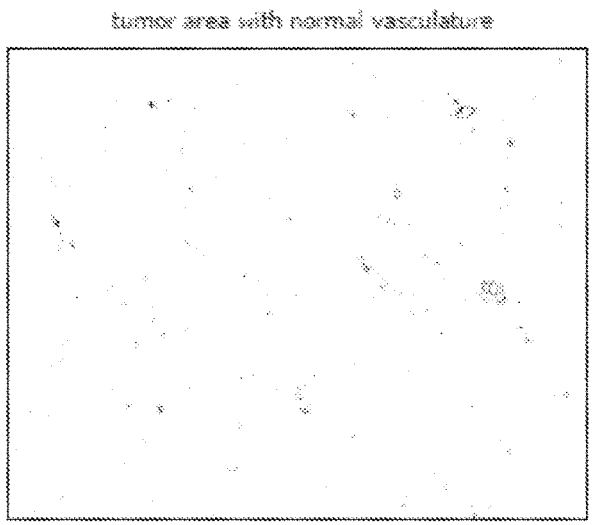
FIGS. 4A and 4B is a pair of photographs from a patient specimen of glioblastomamultiforme showing cells stained for integrin beta 1 expression where there is normal vasculature (4A) and in angiogenicglomeruloid vessels (4B).
Figure 4B:
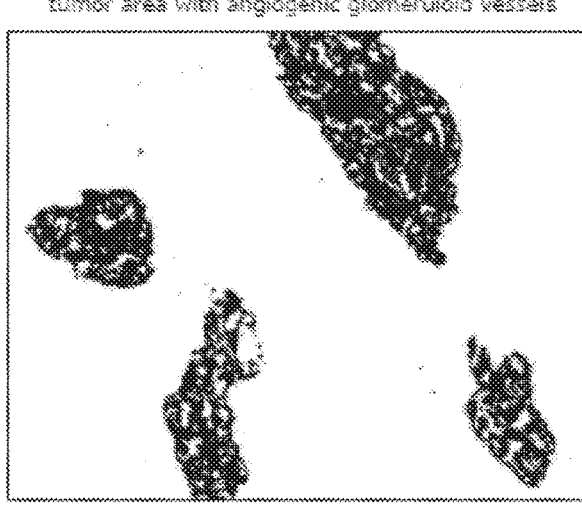

Further increases in beta 1 expression in tumor cells in vitro were observed during tumor cell proliferation itself. There is an inverse correlation between cell confluence in vitro and level of beta 1 in U87MG glioma cells (FIG. 3A). In addition, expression of proliferation marker Ki-67 was positively correlated with beta 1 expression in U87MG glioma cells as demonstrated by FACS (FIG. 3B). This is consistent with what others have observed in breast carcinoma cells. Finally, we visually observed significant increases in beta 1 integrin expression in angiogenic vessels in human surgical specimens from primary GBM (FIG. 4). This increased beta 1 integrin expression is thought to be related to the association of beta 1 to cellular proliferation observed in glioma cells, as discussed above. Thus, in addition to invasion and growth upon vessels, beta 1 integrin appears to be intimately involved in tumor cell proliferation, survival signaling after hypoxia and IR, and in vascular endothelial cells during the process of angiogenesis. These multiple features make beta 1 integrin a highly attractive target to potentially inhibit growth of tumors directly and as a conjunctive therapy with anti-angiogenesis to attenuate development of anti-angiogenic resistance.

Example 3

Beta 1 Integrin Involvement in Anti-VEGF Antibody Resistance in Tumor Cells

To test the hypothesis that beta 1 integrin may be involved in bevacizumab resistance we used immunofluorescent histochemistry for beta 1 integrin in paired patient specimens of GBM taken before bevacizumab therapy and after development of acquired bevacizumabresistance. Clear increases in post-bevacizumab GBM tissues compared to untreated specimens was seen in 9 of 12 pairs (75%, data not shown FIC. 5).

Figure 5:
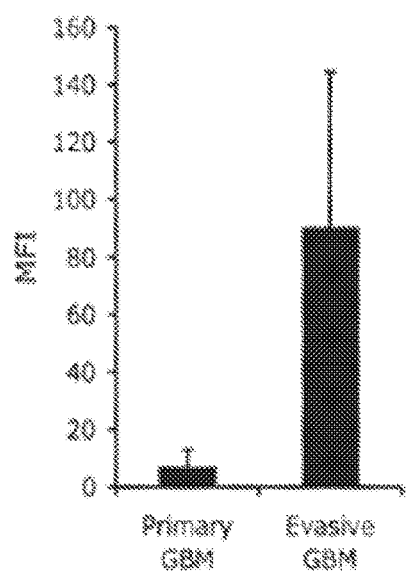
FIG. 5 is a bar graph plotting integrin beta 1 expression in cases of primary glioblastoma and antiangiogenic evasive glioblastoma.

To directly verify the increase in beta 1 integrin expression in tumor cells after acquired bevacizumab resistance we analyzed cell lines derived from primary GBMs (first surgery) and from tissue isolated at least 30 d after development of resistance to antiangiogenic therapy. Indeed, beta 1 integrin expression was an average of 13-fold higher in cells from the latter group compared to the former (FIG. 5).

To verify that the observed beta 1 integrin upregulation was functional we stained adjacent patient tumor sections for activated focal adhesion kinase (phospho-FAK$^{tyr397}$). phospho-FAK$^{tyr397}$ staining was significantly higher in the patient samples taken after acquired bevacizumab resistance compared to samples taken prior to therapy (data not shown).

Thus, beta1 integrin is functionally upregulated in clinical patient samples taken after the development of acquired bevacizumab resistance.

Example 4

Figure 6A:
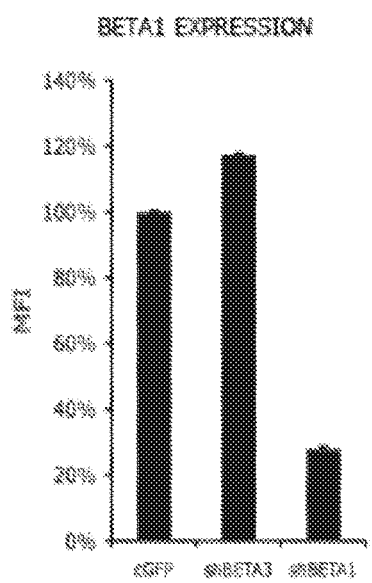
FIGS. 6A and 6B is a pair of bar graphs showing integrin beta 1 expression (6A) and proliferation (6B) of three different knock down cell lines, where the integrin beta 1 knockdown showed substantially less expression and proliferation.
Figure 6B:
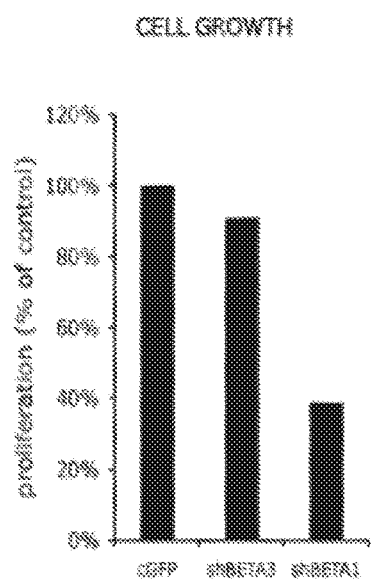

Decreased Aggressiveness in Anti-VEGF Antibody Resistant Cell Lines After Inhibition of Beta1 Integrin Integrin beta 1 shRNA in lentiviral particles were purchased from Santa Cruz Biotechnology, Inc., catalog #sc-35675. A mixture of four different shRNA sequences are provided. This material was used to transform cell line SF8106-Ax1 and SF7796-Ax3 (also known as BRG3 and BRG2, respectively), derived from patients who failed bevacizumab. We created stable knockdown lines of beta 1 and beta 3 integrins using a lentiviral vector. We verified 70% knockdown of beta 1 in the BRG3 cells and a corresponding 60% decrease in cell growth after 1 week compared to either GFP vector control cells or beta 3 knockdown cells (FIG. 6). To study these cells in more detail, we isolated BRG3 knockdown clones with over 90% knockdown of beta 1 and assessed functions indicative of increased tumor cell aggressiveness including adhesion, cell spreading, cell migration, and cell proliferation. These knockdown clones were significantly impaired in all four functions compared to the vector control cells (data not shown).

To verify the above findings in vivo we implanted three of the above BRG3 beta 1 integrin knockdown clones subcutaneously in nude mice and followed tumor growth for 6 months. Vector control tumor cells grew normally whereas we observed no growth of any of the knockdown clones for the entire study period (data not shown). Indeed, 13 of the 15 (87%) knockdown tumors completely regressed. To verify these findings are directly a result of beta 1 knockdown we implanted polyclonal knockdown lines from the BRG2 and BRG3 subcutaneously and similarly monitored growth in vivo. These lines demonstrated an average of 70% beta 1 knockdown. As predicted, these lines grew slower than the vector control lines. However, in contrast to the 90% knockdown clones, after several weeks both lines displayed latent growth in vivo suggesting a dose-response relationship for proliferation and levels of beta 1 integrin (data not shown).

Thus, 90% or greater knockdown of beta1 in bevacizumab resistant glioma lines attenuates aggressive phenotypes in vitro and completely prevents growth in a xenograft model in vivo.

Example 5

Figure 7:
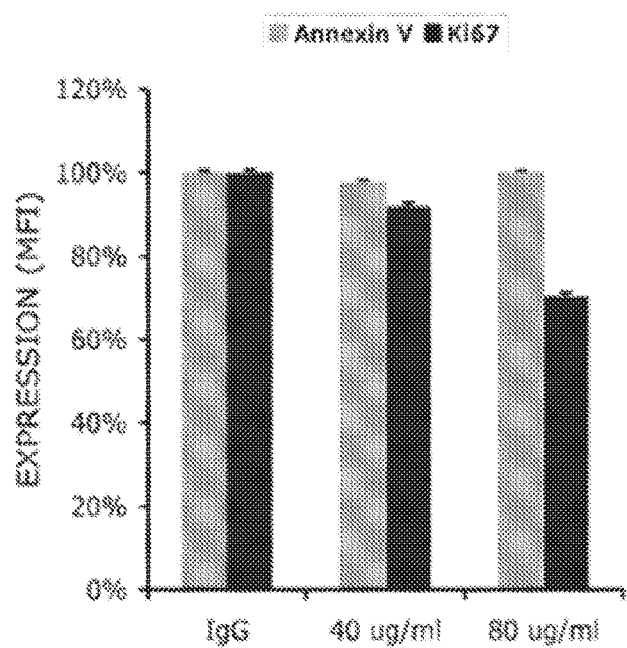
FIG. 7 is a bar graph showing expression of annexin and Ki67 apoptosis markers at different concentrations of AIIB2 in an antiangiogenesis resistant glioblastoma cell line.

Anti Beta 1 Integrin Antibody Treatment of an Anti-VEGF Antibody Resistant Cell Line To verify the above results with a clinically-relevant mode of beta 1 inhibition we used the well characterized AIIB2 inhibitory rat monoclonal anti-beta 1 integrin antibody in in vitro inhibition experiments. An isotype-matched IgG was used as a control. Bevacizumab resistant glioma lines demonstrated similar inhibition of function as beta 1 knockdowns including decreased adhesion (data not shown) and migration (dynamic movie analysis, not shown) at 10 µg/ml. Effects on cell growth were demonstrated with immunofluorescent staining for either apoptosis/cell death (annexin V) or proliferation (Ki-67 antigen). After staining cells were sorted by flow cytometry/fluorescence activated cell sorting (FACS). This analysis demonstrated a significant decrease in Ki-67 staining in GBM cells treated with AIIB2, but no effect on annexin V immunoreactivity, consistent with a cytostatic effect (FIG. 7).

Figure 8:
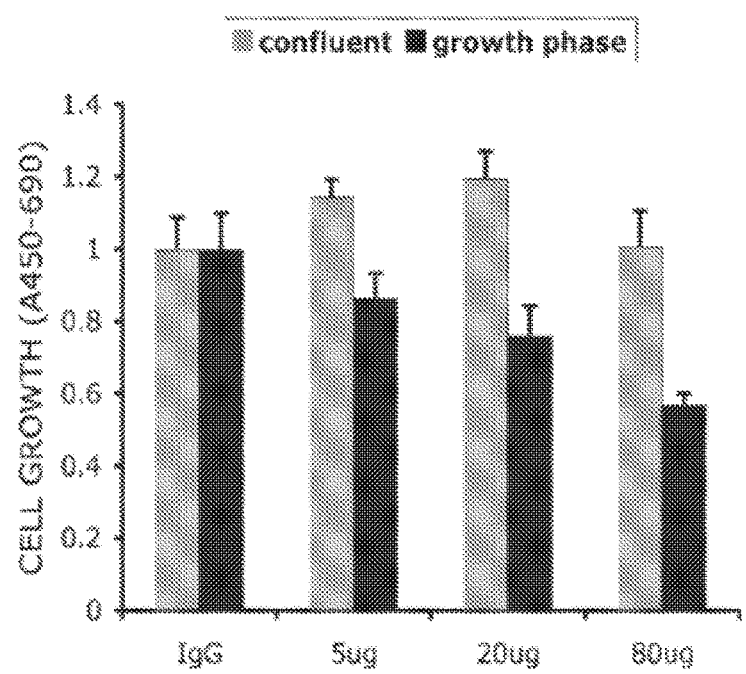
FIG. 8 is a bar graph showing cell growth under different concentrations of AIIB2 antibody of the primary GBM cell line.
Figure 9:
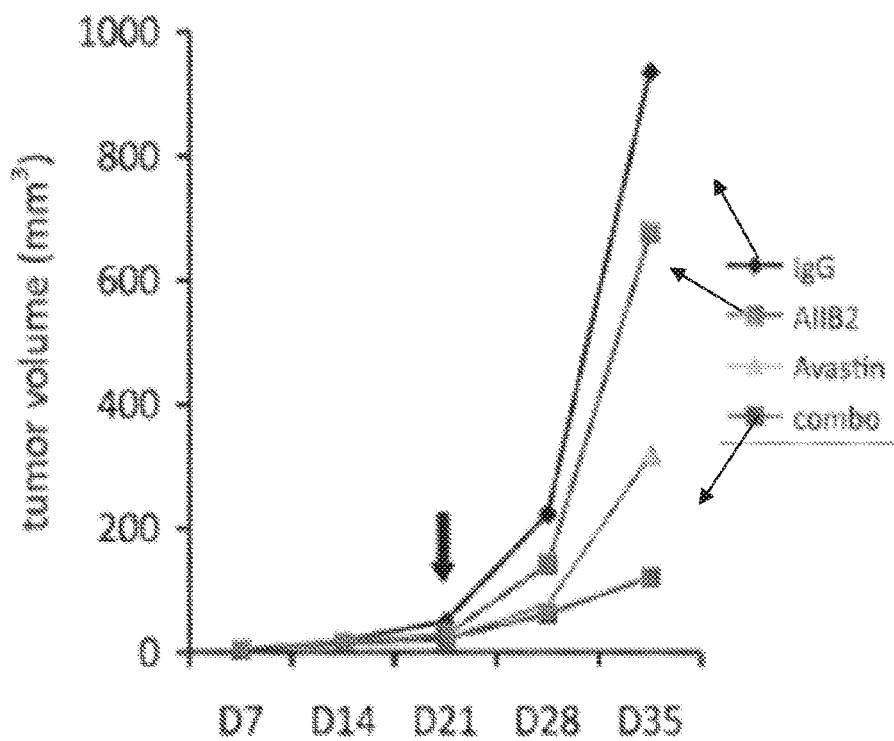
FIG. 9 is a graph showing tumor volume changes under different treatments of antibodies in a mouse tumor model. The plot labeled "combo" is a combination of AIIB2 and bevacizumab. The arrow shows the start of treatment.

This treatment with AIIB2 was repeated with a primary GBM line in vitro to see if cell growth would be affected by proliferative status. Cells in subconfluent culture (growth phase), but not those in confluent culture (growth arrest), were significantly growth inhibited by AIIB2 treatment for 2 days (FIG. 8).

Finally, in vivo treatment with AIIB2 at doses of up to 5 mg/kg twice weekly significantly inhibited growth of the BRG3 bevacizumab resistant line (data not shown) in a subcutaneous xenograft model. Terminal deoxynucleotidyl-transferasedUTP nick end labeling (TUNEL) revealed increased apoptosis in the AIIB2 treated tumors in the BRG3 line (data not shown).

Thus, beta1 integrin inhibition with function-blocking antibodies such as AIIB2 attenuates aggressive phenotypes in vitro similar to beta1 knockdown. In addition, parenteral administration of AIIB2 is effective for inhibiting tumor growth of classic and bevacizumab resistant gliomaxenografts in vivo.

Example 6

Inhibition of Beta1 Reverses Epithelial to Mesenchymal Transition (EMT) and Stem-like Phenotypes Spheroidal tumor cell growth in culture is a surrogate for stem-like phenotype and can be promoted/enriched by stressors such as hypoxia and acid pH. Knockdown of beta1 in both a classic gliomacell line (U87MG) and the BRG3 bevacizumab resistant line significantly impaired spheroid formation (data not shown). AIIB2 also inhibited spheroidal growth of U87MG glioma cells induced by 48 hours of hypoxia (data not shown).

In addition to impairment of spheroidal growth, inhibition of beta1 integrin promoted reversal of EMT as demonstrated by a significant increase in tumor cell area and a 50% decrease in the mesenchymal receptor c-met (data not shown).

Example 7

Potentiation of Antiangiogenic Therapy with Beta1 Integrin Inhibition

Figure 10:
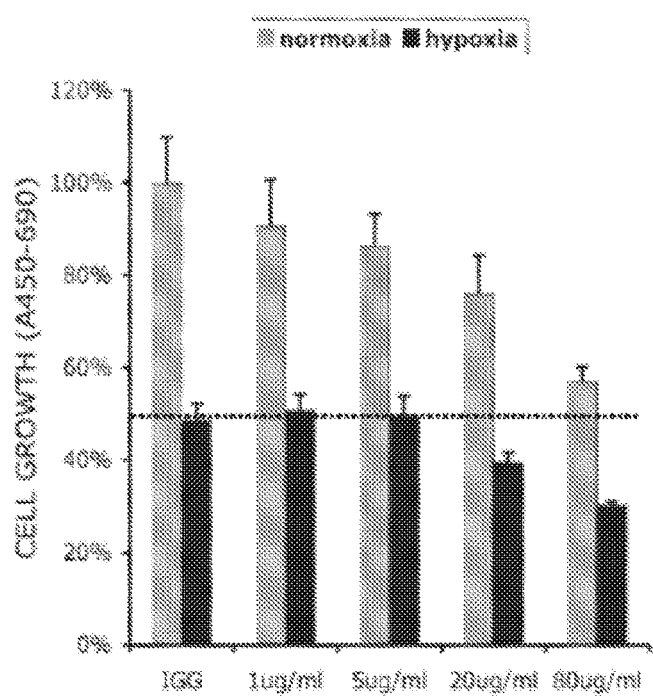
FIG. 10 is a bar graph showing cell growth over time of GBM cells subjected to hypoxia for 2 days followed by growth at normoxia. Cells were given IgG (control) and different concentrations of AIIB2

As an in vitro model of the effects of antiangiogenic therapy we subjected growth phase primary GBM cells to hypoxia for 2 days followed by continued growth in normoxia for 2 days. Hypoxia is used as an in vitro surrogate for anti-angiogenesis therapy such as bevacizumab. The addition of AIIB2 antibodies for the 2 day recovery period resulted in a further decrease in tumor cell growth as compared to either hypoxia or AIIB2 treatment alone (FIG. 10). Thus, the combination of beta 1 integrin inhibition with anti-angiogenesis is predicted to potentiate therapeutic efficacy.

Figure 11:
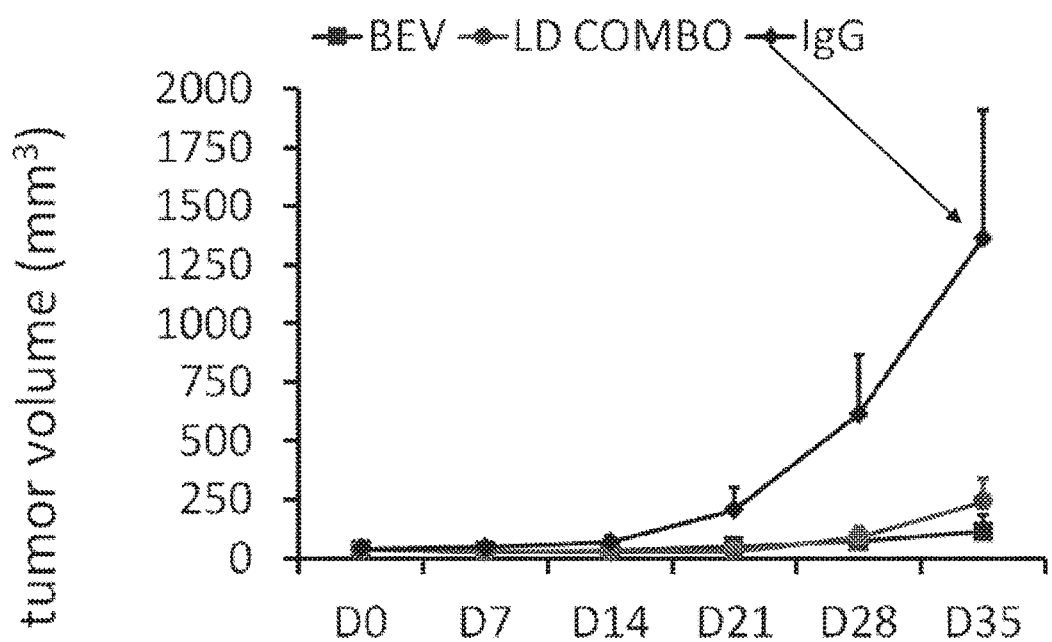
FIG. 11 is a line graph showing tumor growth over time for U87MG glioma tumors measured biweekly with control IgG (10 mg/kg) (diamonds), bevacizumab (10 mg/kg) (squares), or low-dose alternating combination therapy of bevacizumab (1 mg/kg) and AIIB2 (1 mg/kg) (circles).

To verify the in vitro results above we treated mice with growing subcutaneous U87MG glioma tumors biweekly with control IgG (10 mg/kg), bevacizumab (10 mg/kg), or low-dose alternating combination therapy of bevacizumab (1 mg/kg) and AIIB2 (1 mg/kg). After several weeks of treatment, the low-dose alternating combination therapy proved to be as effective for inhibition of tumor growth as standard dose bevacizumab alone (FIG. 11). Thus, beta 1 integrin inhibition with AIIB2 allowed a 20-fold decrease in bevacizumab dose.

Thus, in summary, it is shown that inhibition of beta1 integrin may inhibit growth of tumors by 1) preventing vessel co-option and perivascular invasion (or invasion upon any classical ECM substrate), 2) reducing viability of tumor cells after insults such as IR and hypoxia possibly by promoting apoptosis, 3) directly inhibiting tumor cell proliferation, 4) directly inhibiting angiogenesis by targeting proliferating and migrating endothelial cells and 5) reversing the aggressive stem-like phenotype including epithelial to mesenchymal transition (EMT). Importantly, antagonizing the beta1 receptor via either lentiviral knockdown or with AIIB2 can significantly attenuate growth of bevacizumab-resistant gliomaxenograftsin vivo. Further, AIIB2 treatment can reduce the necessary dose of bevacizumab up at least 20× in a gliomaxenograft model.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

What is claimed is:

1. A method for attenuating the development of bevacizumab resistance in a subject having glioblastoma and having received bevacizumab to treat the glioblastoma, comprising:
administering a therapeutically effective amount of an anti-integrin beta-1 antibody which binds to a beta-1 subunit of an integrin having any alpha subunit to a subject having glioblastoma and having received bevacizumab to treat the cancer,
to attenuate the development of bevacizumab resistance in the subject,
wherein the anti-integrin beta-1 antibody is the AIIB2 antibody or a humanized version thereof.

2. The method according to claim 1, wherein the anti-integrin beta-1 antibody is administered parenterally.

3. The method according to claim 1, wherein the anti-integrin beta-1 antibody is administered intratumorally.

4. The method according to claim 1, wherein the anti-integrin beta-1 antibody is administered through a catheter via a convection enhanced delivery (CED) device.

5. The method according to claim 1, wherein the anti-integrin beta-1 antibody is a humanized version of the AIIB2 antibody.

6. The method according to claim 1, wherein the anti-integrin beta-1 antibody is the AIIB2 antibody.

* * * * *

UNITED STATES PATENT AND TRADEMARK OFFICE
CERTIFICATE OF CORRECTION

PATENT NO. : 11,185,585 B2
APPLICATION NO. : 15/869970
DATED : November 30, 2021
INVENTOR(S) : Warren Shawn Carbonell et al.

It is certified that error appears in the above-identified patent and that said Letters Patent is hereby corrected as shown below:

In the Specification

In Column 1, Line 62, please change "379:2103-" to -- 370:2103- --;

In Column 5, Line 17, please change "fit-1" to -- flt-1 --;

In Column 9, Line 44, please change "hearing" to -- bearing --;

In Column 10, Line 22, please change "Marine" to -- Murine --;

In Column 10, Line 23, please change "Atwell" to -- Ancell --;

In Column 10, Line 63, please change "BIE11" to -- BIEII --;

In Column 11, Line 19, please change "AIIB2also" to -- AIIB2 also --;

In Column 13, Line 22, please change "179" to -- 479 --;

In Column 14, Line 10, after "Agent" please add -- which --;

In Column 14, Line 35, please change "(EGER)" to -- (EGFR) --;

In Column 14, Line 46, please change "hind" to -- bind --;

In Column 15, Line 9, before "be" please add -- will --; and

In Column 17, Line 55, please change "(75%, data not shown FIC. 5)." to -- (75%, data not shown). --.

Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*